United States Patent [19]

Lavaux

[11] Patent Number: 5,352,445
[45] Date of Patent: Oct. 4, 1994

[54] LAVAUX TEAR TEST LACRIMAL EQUILIBRATION TIME (LET)

[76] Inventor: Joseph E. Lavaux, 608 E. Harmony Rd., Fort Collins, Colo. 80525

[21] Appl. No.: 879,330

[22] Filed: May 7, 1992

[51] Int. Cl.$^5$ ............................................. A61K 31/715
[52] U.S. Cl. .................................. 424/78.04; 604/264; 604/267; 514/915
[58] Field of Search ................ 424/78.04, 427; 604/264, 267; 514/915

[56] References Cited

U.S. PATENT DOCUMENTS

| | | | |
|---|---|---|---|
| 4,839,342 | 6/1989 | Kaswan | 514/915 |
| 5,006,310 | 4/1991 | Gin et al. | 435/805 |
| 5,041,434 | 8/1991 | Lubkin | 514/182 |

FOREIGN PATENT DOCUMENTS 2169508  7/1986  United Kingdom ............... 514/915

OTHER PUBLICATIONS

Rieger Klin. Monat Aug. 1987 Feb:190(2) 135-8.
Hawkins et al Mar. 1 (188)(5) J. Am. Vet Med. Assoc. 1986 511-3.
Pandher et al Acta Ophthalmol Dec. 1985; 63(6) 695-7.

*Primary Examiner*—Thurman K. Page
*Assistant Examiner*—Peter F. Kulkosky

[57] ABSTRACT

A method for measuring precorneal tear film stability and diagnosing dry and wet eye conditions. The method comprises stressing baseline visual acuity with the installation of a predetermined ophthalmic preparation and measuring the time to recover normal visual acuity. Once baseline visual acuity is regained and sustained, the Lacrimal Equilibration Time (LET) is recorded. LET measures the quality of precorneal tear film stability and is related to the degree of dry and wet eye condition.

3 Claims, No Drawings

LAVAUX TEAR TEST LACRIMAL EQUILIBRATION TIME (LET)

FIELD OF THE INVENTION

This invention relates to a method for testing precorneal tear film stability. It relates to a process to aid in the diagnosis of diseases of the eye surface and of the lacrimal system. More specifically, it tests dry and wet eye conditions. Precorneal tear film stability is also useful for predicting candidates who might be successful contact lens wearers.

BACKGROUND OF THE INVENTION

A stable preocular tear film is essential for maintenance of a healthy and comfortable ocular surface as well as for good vision. An unstable preocular tear film results from inadequate or excessive tear production and from inadequate blink force improperly mixing the tear constituents. The ability to quantitatively measure tear film inadequacy is important to the diagnosis and management of dry and wet eye conditions.

DESCRIPTION OF THE PRIOR ART

There are a number of tests which describe methods of measuring preocular tear film stability. None of the tests are definitive in a differential diagnosis of dry and wet eye conditions. They only lend supportive evidence for diagnosing these conditions.

Schirmer tear test is a tear production test using a strip of wettable filter paper inserted into the lower conjunctival fornix. An assessment of tear production is made based on the length of wetness of the strip over a five minute time. This test is invasive, potentially dangerous to the corneal surface, inaccurate due to inter and intra subject variation of tear flow and the results are controversial among eye car practitioners.

Break up time (BUT) test is a tear integrity test. The time interval between the blink and the first observable dry spot of the corneal surface is related to tear integrity. The test requires sodium fluorescein which disrupts the tears and leads to inaccurate results. The test is limited by the skill, experience and subjectivity of the observer. It requires the use of expensive equipment, namely a biomicroscope which projects a bright light which may cause reflex tearing. It also tests during an abnormal state since the eyes must remain open beyond the normal blink rate.

Tear thinning time (TTT) test is a test of tear integrity. The time interval between the blink and the first observable distortion of the reflected mire from a keratometer is related to tear integrity. This test requires the use of expensive equipment, a keratometer, and is limited by observer experience. The test is also limited in that it tests a very small area of the preocular tear surface. It tests during an abnormal state since the eye must remain open beyond the normal blink rate.

Tear meniscus Height (TMH) is a tear production test. It assesses the amount of tear by the height of tear meniscus between the eye surface and the lower lid. It requires expensive equipment, namely a biomicroscope with a bright light which could stimulate reflex tears. Additional tears would cause inaccurate results. It is also limited by the experience and subjectivity of the observer.

Lipid layer thickness test is a specific test about the external lipid layer of the tear film. Deficiencies of this layer could enhance tear evaporation and thus create a risk for dry eye condition. The test is not specific nor dry eye but indicates dry eye conditions indirectly when the lipid layer is not seen. The test is limited by the experience of the observer. It also requires expensive equipment, namely a biomicroscope.

Dye tests such as Rose Bengal and Sodium Fluorescein will detect tissue destruction. When the tissue shows destruction, one can conclude a potential loss of mucin, the inner layer of the tear film. Since mucin is responsible for the maintenance of the tear film over the eye surface, dry eye symptoms may be present. This test does not provide quantitative or qualitative tear film measurements. It requires the expensive biomicroscope and an experienced observer.

Punctum plug test obstructs the drainage of tear from the eye surface. Therefore, if one has dry eye symptoms from insufficient tear production, more tears should remain on the eye surface when drainage is obstructed. That in turn should result in some amelioration of the dry eye symptoms. This test does not provide qualitative measurements, just indirect quantitative tear production via patient symptoms or signs of improvement several days into the test. The test is limited by the skill and experience of the practitioner. It is invasive and expensive requiring considerable practitioner skill, time and expensive equipment, namely the biomicroscope.

Lactoplate test assesses the lacrimal gland function by the amount of lactoferrin it produces in the tear film. The test uses a filter paper which is placed on the eye to absorb the tear with the lactoferrin. The amount of lactoferrin is assessed using an immunodiffusion technique. The test is invasive and is limited by the experience of the examiner. It is expensive and requires two or three days to determine if the lacrimal gland is functioning normally. This test uses indirect assessment of the aqueous tear layer and is not conclusive for all dry eye conditions.

Agar diffusion lysozyme test differs from the lactoplate test only by the product which the lacrimal gland secretes. It possesses the same benefits and disadvantages.

Conjunctival scraping and impression cytology assesses the goblet cell density which determines the amount of mucin secretion. It is invasive and is neither quantitative nor qualitative toward tear film stability. It requires an experienced practitioner and expensive equipment.

DESCRIPTION OF THE INVENTION

The invention, Lavaux tear test, Lacrimal Equilibration Time Test (LET), assesses preocular tear film stability. Visual acuity is measured with standard tests such as: a snellen chart, Landolt C or tumbling E chart, or other such character type charts or contrast sensitivity tests. This measurement, then becomes the normal or standard visual acuity one relates to during the test. An ophthalmic preparation, such as carboxymethylcellulose, the principal ingredient of Celluvisc ® ophthalmic solution manufactured by Allergan Pharmaceutical, is then added to the preocular tear film.

Due to the viscosity of this preparation, visual acuity becomes blurred. The subject resumes normal blinking and eye movements during the test. If the subject is capable of normal tear film stability, adequate tear production, adequate blink force and sufficient drainage, the preparation will be eliminated via the lacrimal drainage system from the preocular surface within a reasonable time. The time required for visual acuity to return to normal becomes the Lacrimal Equilibration Time (LET). The LET time is then used to diagnose normal and abnormal tear film stability. Using one drop of carboxymethylcellulose per eye, normal LET is considered to be 5 minutes or less. LET times longer than 5 minutes detects subjects with unstable tear film. This includes subjects with inadequate aqueous tear production, inadequate blink force and/or inadequate tear drainage. Thus the Lavaux tear test detects both qualitatively and quantitatively dry and wet eye subjects.

The Lavaux Tear Test, Lacrimal Equilibration Time (LET) is easily administered. With minor training or simple written instructions, ancillary personnel and lay people can administer the test in a practitioner's office or off-site in a variety of facilities. The test is performed under normal eye conditions and is non-invasive and safe, since the ophthalmic preparation is soothing and comfortable to the eye. The ophthalmic preparation is readily available and quite inexpensive. The LET is quick, since the results are observable within five minutes.

EXAMPLE 1

This example sets forth a generalized procedure for this dry eye test and results.

Twenty patients were selected from my practice without regard to age or sex. Their average age was 52 and ranged from 17 to 77 years of age. There were 7 males and 13 females. None of the patients were currently wearing contact lenses or presenting microbial infection. An attempt was made to include 12 symptomatic patients as well as 8 asymptomatic patients. Subjects were selected over a two month period from patients seeking routine care as well as from patients who had been previously diagnosed as symptomatic dry eye patients. I either performed or directly supervised the performance of all subject testing.

For each patient the best snellen visual acuity of both eyes was measured at 20 feet. Patients used their glasses if needed for better VA. This acuity was used as the base-line standard and patients were instructed to relate to this standard throughout the test. Patients were asked to assume an upward gaze, the lower lid was gently depressed and one drop of Celluvisc ® was instilled into the lower conjunctival sac of the right followed by the left eyes. Care was practiced to minimize expression of lower lid meibomian and accessary gland secretions as well to avoid creating patient anxiety. A stop watch was switched on when the Celluvisc ® was instilled and was switched off when the subjects base-line VA was regained and sustained after normal blinks. This time interval became the Lacrimal Equilibration Time (LET). Subjects were instructed not to force blinking or wipe their eyes in an effort to hasten the removal of the drop for early resumption of base-line VA. Patients remained in the examination chair without restriction of eye movements. During the test time, patients were questioned about possible dry and wet eye symptoms or engaged in "small talk" to distract them from focusing on visual clarity. After at least 20 minutes, each patient received a Schirmer I test under anesthesia by a single drop of 0.5% proparacain OU.

RESULTS AND DISCUSSION

Data representing age, sex, LET times, Schirmer times and presence of dry eye symptoms for all 20 patients are presented in Table 1. The findings of the Schirmer tear test showed less tear production with advancing age. The findings of the LET test also showed longer times with advancing age. Both lower Schirmer test and longer LET times showed a direct correlation with aging and thus with each other. The LET test identified symptomatic patients as those patients requiring over 5 minutes to complete the test. Completion of the test was defined as reaching base-line VA. Asymptomatic patients completed the test in less than 5 minutes.

The LET test involves the entire lacrimal system, tear production, tear mixing by blinking and tear elimination. A drop of Celluvisc ® to the tear disturbs both the normal visual acuity and tear volume. High LET results may be due to one of three reasons: (1) A poor flushing mechanism of the aqueous layer may exist. (2) High LET times may be a result of poor tear elimination of the tears via the lacrimal drainage system and (3) High Let times may be a result of inadequate blink force.

CONCLUSIONS

The LET offers an alternative to currently available dry eye tests. It correlates highly with dry eye symptoms. It offers significant advantages to the practitioner since it uses readily available materials, as easily administered by clinicians and their ancillary personnel and can be performed off-site by persons with minimal training. In this study the LET test results were at least as reliable as the more invasive Schirmer test in assessing tear production. It demonstrated superior results over the Schirmer test in detecting symptomatic patients. It may also be useful for detecting inadequate tear elimination via the lacrimal drainage system and inadequate blink force.

The LET test may prove to be the easiest, least invasive, quickest, most reliable and most cost effective dry eye test currently available to the eye care practitioner.

TABLE 1

| Collected data of twenty Patient tests. | | | | | |
|---|---|---|---|---|---|
| Age | Sex | OD-Schirmer-OS | | OD--LET--OS | | Symptoms |
| 17 | F | 17.00 | 16.00 | 1.75 | 1.75 | 0 |
| 26 | F | 15.00 | 13.00 | 1.50 | 1.25 | 0 |
| 27 | F | 7.50 | 10.00 | 10.00 | 11.50 | Y |
| 31 | F | 13.00 | 13.00 | 3.50 | 3.75 | 0 |
| 32 | M | 17.00 | 17.00 | 3.25 | 3.25 | 0 |
| 35 | F | 5.50 | 10.00 | 1.00 | 1.50 | 0 |
| 38 | F | 8.00 | 11.00 | 10.50 | 9.00 | Y |
| 40 | F | 13.00 | 14.00 | 1.50 | 0.67 | 0 |
| 44 | F | 3.50 | 3.50 | 10.00 | 8.50 | Y |
| 46 | F | 2.00 | 9.00 | 12.00 | 12.00 | Y |
| 49 | F | 20.00 | 19.00 | 5.00 | 3.00 | 0 |
| 64 | M | 5.00 | 8.00 | 15.00 | 15.00 | Y |
| 70 | M | 3.50 | 7.00 | 14.00 | 11.00 | Y |
| 71 | F | 14.00 | 13.00 | 13.00 | 15.00 | Y |
| 71 | M | 15.00 | 15.00 | 6.00 | 6.00 | Y |
| 73 | M | 6.00 | 15.00 | 5.50 | 5.50 | Y |
| 74 | F | 5.50 | 0.00 | 4.50 | 4.00 | 0 |
| 75 | M | 13.00 | 13.00 | 15.00 | 15.00 | Y |
| 76 | F | 2.50 | 0.00 | 15.00 | 5.75 | Y |
| 77 | M | 5.50 | 6.00 | 10.00 | 10.00 | Y |
| AVERAGE | | | | | | |
| 51.80 | | 9.58 | 10.63 | 7.90 | 7.17 | |
| STANDARD DEVIATION | | | | | | |
| | | 5.50 | 5.16 | 4.94 | 4.76 | |

The test results shown herein, as well as other data collection still in progress, show the benefits of this invention for the identification of persons possessing inadequate precorneal tear film stability. The above example is not intended to be all inclusive or to limit in any way the application of the invention or the scope of the appended claims.

What is claimed is:

1. A method of accessing precorneal tear film stability, including symptomatic dry and wet eye conditions, comprising topically applying into the eye a predetermined topical ophthalmic preparation that is visually blurring comprising carboxymethylcellulose sodium 1%, calcium chloride, potassium chloride, purified water, sodium chloride and sodium lactate said eye so treated visually clearing over a period of time by tear film production, tear mixing by the blink force and tear elimination by evaporation and drainage, wherein said period of time measures a precorneal tear film stability and said period of time for visual clearing is substantially longer when dry and wet eye symptoms occur.

2. The method of claim 1 wherein said visual blurring and clearing is measured by Snellen visual acuity charts or other visual acuity tests used by eyecare professionals.

3. The method of claim 1 comprising use for determining eye surface health, comfort and lubrication, lowered visual acuity or eye surface disorders.

* * * * *